United States Patent [19]
Sorenson

[11] 4,106,621
[45] Aug. 15, 1978

[54] COMBINATION NEEDLE COVER AND VENIPUNCTURE DEVICE TRAY AND METHOD OF USING SAME

[75] Inventor: James L. Sorenson, Salt Lake City, Utah

[73] Assignee: Sorenson Research Co., Inc., Salt Lake City, Utah

[21] Appl. No.: 708,968

[22] Filed: Jul. 26, 1976

[51] Int. Cl.² .................. B65D 73/00; B65D 75/62; B65D 83/02
[52] U.S. Cl. ................................ 206/365; 206/461; 206/469; 206/470; 206/624
[58] Field of Search .................. 128/184, 215, 218 R, 128/218 S; 206/364–365, 367, 461, 467, 469–470, 498, 525, 532, 804; 229/44 R

[56] References Cited
U.S. PATENT DOCUMENTS

| 2,892,538 | 6/1959 | Middleton, Jr. et al. ........ 206/469 X |
| 3,035,691 | 5/1962 | Rasmussen et al. .................. 206/364 |
| 3,074,540 | 1/1963 | Beich et al. ........................ 206/469 X |
| 3,075,639 | 1/1963 | Lingley .............................. 206/469 X |
| 3,472,368 | 10/1969 | Hellstrom ............................ 206/469 |
| 3,889,808 | 6/1975 | Helms ................................ 206/469 X |
| 3,967,730 | 7/1976 | Driscoll et al. ..................... 206/470 X |

FOREIGN PATENT DOCUMENTS 1,474,882  2/1967  France ..................................... 206/365

Primary Examiner—Steven E. Lipman
Attorney, Agent, or Firm—H. Ross Workman; J. Winslow Young

[57] ABSTRACT

A venipuncture device package which when opened serves as a combination needle cover and venipuncture device tray from which a venipuncture device may be withdrawn or inserted with one hand without having to apply any force to the package. In one preferred embodiment, a blister cover made of ductile plastic is configurated to form a venipuncture device tray which is separably joined to a strip of paper backing to form the package. The tray is constructed so as to facilitate angular deformation of the tray into a hand-displaceable needle cover once the strip of paper has been partially peeled away to expose the handle of the venipuncture device while maintaining the needle of the venipuncture device enclosed within the package. In other presently preferred embodiments, the tray is constructed so that it may be broken open at a predetermined location so as to form a hand-displaceable needle cover having the handle of the venipuncture device exposed while maintaining the needle of the venipuncture device enclosed within the package. The method of using the preferred embodiments is also disclosed.

5 Claims, 8 Drawing Figures

COMBINATION NEEDLE COVER AND VENIPUNCTURE DEVICE TRAY AND METHOD OF USING SAME

BACKGROUND

1. Field of the Invention

The present invention relates to needle covers for venipuncture devices and more particularly to a package having novel structure whereby the package, when opened forms a combination needle cover and venipuncture device tray.

2. The Prior Art

Historically, venipuncture devices of a type having a needle portion and a handle portion have had a separate cover for protecting and enclosing the needle portion of the venipuncture device. Typically, a needle cover for a venipuncture device fits over the needle of the venipuncture device and is press-fit onto the hub of the needle, the press-fit relation between the cover and the hub thereby insuring that the cover will not slip off the needle of the venipuncture device without applying sufficient pressure with the thumb and forefinger to push the cover off the needle hub. This type of venipuncture device complete with its needle cover is then placed in some type of packaging, generally of a plastic type, enclosing the entire venipuncture device and needle cover until such time as it is desired to use the device.

When using a venipuncture device of the type described above, the venipuncture device is removed from the package and placed on a nearby flat surface. The person using the venipuncture device then prepares the patient's arm for injection of the venipuncture device by sterilizing the skin where the device is to be injected and by palpating the patient's arm with one hand in order to locate the patient's vein. While thus holding the patient's arm in one hand and palpating it so as to locate the patient's vein, the person using the venipuncture device then must pick up the venipuncture device with his other hand and remove the needle cover. Since the needle cover is in press-fit relation with the hub of the needle, considerable force is required to push the cover off of the needle. This causes inconvenience to the person trying to perform the venipuncture and distracts his attention thereby causing him to occasionally lose the location of the patient's vein.

Furthermore, it often happens that while holding a patient's arm in one hand the venipuncture device must be withdrawn from the patient's arm by the other hand and set back down on a nearby surface. In order not to contaminate the needle of the venipuncture device, it is then necessary to place the needle of the venipuncture device back into the needle cover. However, this is inconvenient and oftentimes very difficult to do with one hand since a conventional needle cover is generally of a small tubular shape and the venipuncture needle is two or three inches long. Thus, when a needle cover is lying on a flat surface, it is extremely difficult and inconvenient to replace the relatively long venipuncture needle back into its cover using only one hand, as is often the case.

In addition to the difficulties mentioned above, having to provide a separate needle cover as well as a package for the entire venipuncture device increases the cost involved.

Until this present invention, a single package having novel structure accommodating use of the package when opened as a one-hand-operable combination sterile needle cover and venipuncture device tray has not been available.

BRIEF SUMMARY AND OBJECTS OF THE INVENTION

The present invention comprises novel apparatus and method whereby a package for a venipuncture device may be utilized when opened as a combination sterile needle cover and venipuncture device tray. The package is constructed in part of a ductile plastic material which allows the package to be angularly deformed. When opened and subsequently angularly deformed, the combination needle cover and venipuncture device tray maintains the needle portion of a venipuncture device enclosed within a portion of the sterile package, while at the same time fully exposing the handle portion of the venipuncture device so as to facilitate finger access to the handle. The combination needle cover and venipuncture device tray further comprises novel structure whereby the venipuncture device may then be withdrawn from the package with one hand without having to apply any force to the package to withdraw the device. Similarly, the venipuncture device may also be conveniently reinserted into the needle cover formed by the package in the angularly deformed position using only one hand.

It is therefore a primary object of the present invention to provide novel structure and method for providing a covering for the needle portion of a venipuncture device from which the needle may be selectively withdrawn and reinserted using only one hand without having to apply significant force to remove or replace the cover on the needle portion of the venipuncture device.

It is another primary object of the present invention to provide a method and structure for holding a venipuncture device so as to maintain the needle portion of the device enclosed while at the same time fully exposing the handle portion of the venipuncture device to finger access.

It is another object of the present invention to provide structure and method whereby the combination needle cover and venipuncture device tray may be angularly deformed so as to fully expose the handle portion of the device to finger access and so as to permit the combination to be self-supporting on a flat surface.

It is yet another primary object of the present invention to provide one package for the entire venipuncture device which may be used when closed as the package for the entire device and which may be used when opened and angularly deformed as a combination needle cover and device tray.

These and other objects and features of the present invention will become more fully apparent from the following description and appended claims taken in conjunction with the accompanying drawings.

DETAILED DESCRIPTION OF THE PREFERRED EMBODIMENTS

The invention is best understood by reference to FIGS. 1–8, wherein like parts are designated with like numerals throughout. Although the present invention has application to a variety of different types of needles and syringes, the following description relates to venipuncture devices, which are exemplary of the type of application in which the invention may be utilized. The term venipuncture device is herein defined to include any needle, catheter, syringe or the like used to penetrate human tissue to deliver or access fluids, or the like.

1. Method and Structure of the Embodiment of FIGS. 1-3

Figure 1:
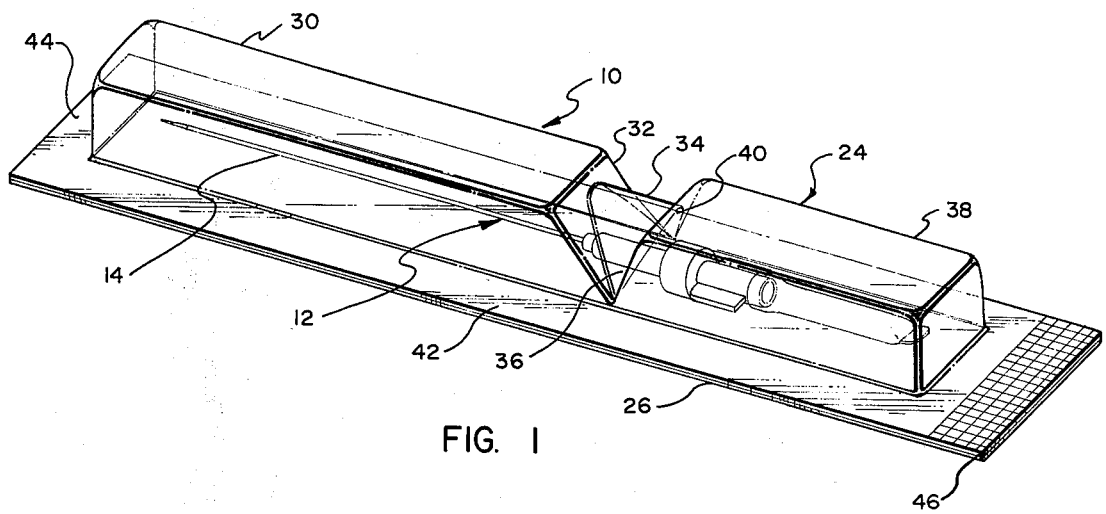
FIG. 1 is a perspective illustration of one presently preferred embodiment of a package for carrying a venipuncture device.

FIG. 1 illustrates a venipuncture device generally designated 12 enclosed within a package generally designated 10. As shown best in FIG. 3, the venipuncture device 12 has a needle portion 14, a hub portion generally designated 16 attached to the rearwardly projecting end of the needle portion 14 and a reflux bulb handle 18 mounted in press-fit relation over the rear end of the hub portion 16. In some venipuncture device embodiments, only a cannula and cannula hub will be packaged. The term "handle" as used herein means the portion of the cannula which is held in the fingers to cause the cannula to penetrate the human tissue. The needle portion 14 has a hollow metallic needle (not shown) which projects telescopically forward through a thin teflon catheter (not shown) which forms a radiopaque sheath over the needle portion 14. The rear end of the radiopaque teflon catheter (not shown) is attached at its rear end to a catheter hub 22. The hollow metallic needle (not shown) of the needle portion 14 extends through the catheter hub 22 and is attached at its rear end to the needle hub 20. As will be hereinafter more fully described, after the needle portion 14 has been injected into a patient's arm, the needle hub 20 may then be detached from the catheter hub 22 so as to free the catheter hub 22 from the rest of the venipuncture device 12. The hollow metal needle (not shown) may then be withdrawn from the patient's arm through the teflon catheter (not shown) leaving only the catheter portion of the venipuncture device 12 in the patient's arm.

As pointed out above, the package 10 of the present invention could be utilized with any one of a number of different types of needles or syringes. Thus, the venipuncture device 12 described above is merely illustrative of one type of device with which the package 10 of the present invention may be utilized, as will hereinafter be described. A venipuncture device such as that described above with which the package 10 of the present invention may be used is the Vinca II which can be purchased from Sorenson Research Co., Inc. at 4387 Atherton Drive, Salt Lake City, Utah.

Figure 3:
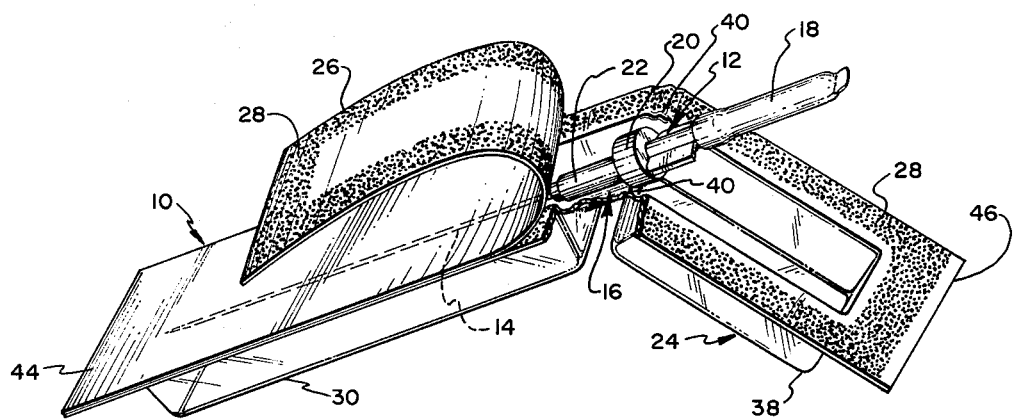
FIG. 3 is a perspective view of the embodiment of FIG. 1 having a portion of the package broken away and illustrating the opening and angular deformation of the package so as to permit its use as a combination needle cover and venipuncture device tray.

Referring again to FIG. 3, it will be seen that the package 10 has a top blister cover configured to form a venipuncture device tray generally designated 24 made of transparent, essentially ductile plastic. A thin strip of paper backing 26 is peelably joined to the bottom of the tray 24 by an adhesive shown schematically at 28. As shown in FIG. 1, the paper backing 26 is used to completely enclose the entire venipuncture device 12 within the tray 24. As will be hereinafter more fully described, the paper backing 26 may be partially separated from the bottom of the tray 24 as shown in FIG. 3 so as to expose the hub portion 16 and handle 18 of the venipuncture device 12.

Referring now to FIG. 1, it will be seen that the plastic venipuncture device tray 24 has a needle cover 30 of generally square cross-sectional shape which covers the needle portion 14 of the venipuncture device 12. At its trailing end, the needle cover 30 has a downwardly sloping surface 32.

The downwardly sloping surface 32 of the needle cover 30 intersects a handle restraining portion 34 of generally parabolic cross-sectional shape. The handle restraining portion 34 similarly is intersected at its trailing end by a downwardly sloping surface 36 of handle cover 38 of the tray 24. The handle cover 38 has a generally rectangular cross-sectional shape similar to that of needle cover 30 and is used to cover the handle 18 of the venipuncture device 12.

Figure 2:
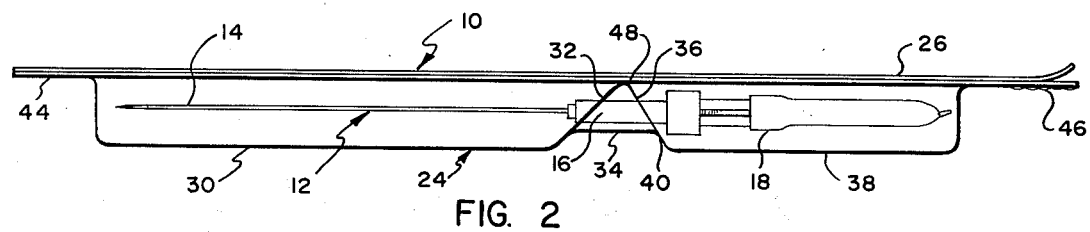
FIG. 2 is a side elevational view of the embodiment shown in FIG. 1 turned upside down in preparation for opening.

From FIG. 2, it will be seen that the sloping surface 32 defined by the trailing end of the needle cover 30 is longer than the sloping surface 36 defined by the leading end of the handle cover 38 of the tray 24. The two sloping surfaces 32 and 36 intersect at 48 in a line at the base of handle restraining portion 34. The difference in length between surfaces 32 and 36 cause the intersection 48 to be displaced from the center of the handle restraining portion 34 slightly towards a rounded shoulder 40. As hereinafter described, the intersection 48 helps to define a predetermined bending location whereby the tray 24 may be angularly deformed at the rounded shoulder 40 when the tray 24 is bent as in FIG. 3.

It should be noted that the rounded shoulder 40 is vertically displaced beneath the top surface of the tray 24. As will be hereinafter more fully described, after the package 10 has been opened and angularly deformed as illustrated in FIG. 3, the handle restraining portion 34 is used to prop up the venipuncture device 12 so as to fully expose the handle 18 of the device 12 to finger access and so as to prevent the venipuncture device 12 from slipping down into the needle cover 30 of the tray 24. The handle restraining portion 34 prevents the venipuncture device 12 from slipping by engaging the needle hub 20 of the venipuncture device 12 with the rounded shoulder 40 of the handle restraining portion 34 as illustrated in FIG. 3.

Furthermore, when the package 10 is in the position illustrated by FIG. 3 the parabolic configuration of the handle restraining portion 34 helps to guide the needle portion 14 of the venipuncture device into the needle cover 30 of the tray 24 when the venipuncture device 12 is being reinserted into the package 10

As shown in FIG. 1, the tray 24 also has a flat peripheral flange 42 circumscribing the needle cover 30, the handle restraining portion 34 and the handle cover 38 of the tray 24. The flat peripheral flange 42 of the plastic tray 24 provides a surface to which the paper backing 26 may be peelably joined by the adhesive 28. The flat peripheral flange 42 also defines surface-engaging ends 44 and 46 at the leading and trailing ends of the package 10. The surface-engaging ends 44 and 46 extend longitudinally past the ends of the needle cover 30 and handle cover 38 of the tray 24 a sufficient distance to permit the surface-engaging ends 44 and 46 to support the package 10 when it is angularly deformed as shown in FIG. 3. As will be hereinafter more fully described, once the tray 24 has been bent at the predetermined location, surface-engaging ends 44 and 46 will then be able to engage a flat surface so as to support the package 10 in a stable manner on the top of the flat surface.

In order to use the package 10 described above as a combination needle cover and venipuncture device tray, the package 10 is first turned upside down as illustrated in FIG. 2. The paper backing 26 is then peeled away from the bottom of the tray 24 beginning at surface-engaging end 46 and continuing until both the handle portion 18 and the hub portion 16 of the venipuncture device 12 are exposed. The paper backing 26 is not peeled away to expose the needle portion 14 of the venipuncture device 12 in order to maintain the needle portion 14 enclosed within the sterile package 10. To insure that the needle portion 14 is maintained enclosed within the needle cover 30, clasps (not shown) or other suitable structure could be used to prevent the paper backing 26 from being separated from the needle cover 30 once the handle 18 of the device 12 has been exposed.

Once the paper backing 26 has been peeled away from the tray 24 as described above, the tray 24 is then bent at the predetermined bending location defined by the intersection 48 of sloping surfaces 32 and 36 and the rounded shoulder 40 located at the trailing end of handle restraining portion 34. As the tray 24 is bent as shown in FIG. 3, the handle 18 of the venipuncture device 12 becomes fully exposed to finger access.

Since the tray 24 is made of ductile plastic, once it has been angularly deformed as shown in FIG. 3, it will maintain the upright configuration as shown. The package 10 may then be placed on a flat surface and it will be held in the illustrated upright configuration by surface-engaging ends 44 and 46.

As described above, while the package 10 is supported on a flat surface in the upright configuration shown in FIG. 3, the venipuncture device 12 is prevented from slipping down into the needle cover 30 of the tray 24 by the small rounded shoulder 40 located at the trailing end of the handle restraining portion 34 which engages the needle hub 20 of the venipuncture device 12. In this manner, the venipuncture device 12 is maintained in a readily accessible position.

Since the handle restraining portion 34 and needle cover 30 have cross-sectional areas substantially larger than the circumference of the hub portion 16 and needle portion 14 of the venipuncture device 12, the device 12 may be readily withdrawn or reinserted into the package 10 without having to apply any force to the package 10 to remove the device 12. This allows the person using the venipuncture device 12 to concentrate his full attention on the venipuncture procedure since his attention is not diverted by having to struggle with the removal of a conventional needle cover placed in press-fit relation onto the needle hub 20. Thus, it can be seen that when opened and angularly deformed as described above, the package 10 of the present invention can be used as a combination sterile needle cover and venipuncture device tray.

2. Method and Structure of the Embodiment of FIGS. 4 and 5

Figure 4:
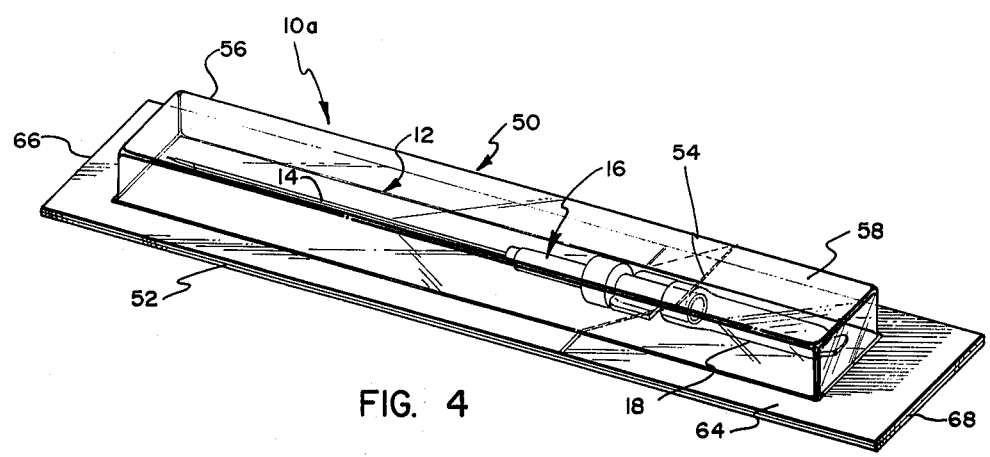
FIG. 4 is a perspective view of a second presently preferred embodiment of the present invention.

The embodiment shown in FIG. 4 illustrates a sterile package 10a having enclosed within it the venipuncture device 12 described above. Package 10a has a top blister cover configurated to form a venipuncture device tray generally designated 50 made of ductile, transparent plastic which is joined to a strip of paper backing 52 by an adhesive (not shown).

Figure 5:
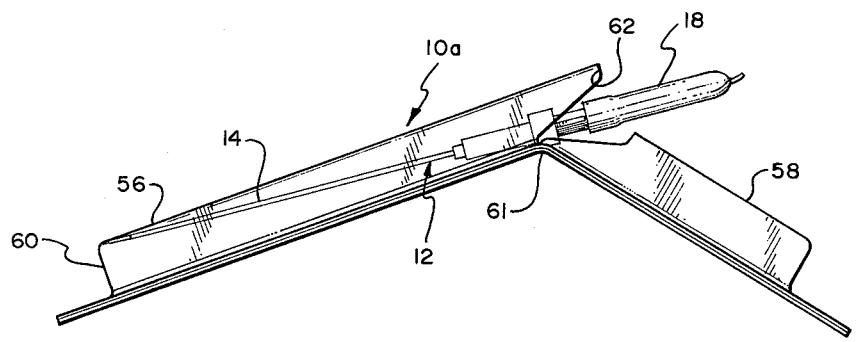
FIG. 5 is a side elevational view showing the embodiment of FIG. 4 opened and angularly deformed so as to permit its use as a combination needle cover and venipuncture device tray.

The tray 50 has a single raised portion of generally rectangular cross-sectional shape which covers the entire venipuncture device 12. A thin line 54 is scribed across the periphery of the raised portion of the tray 50 thereby defining a needle cover 56 for enclosing the needle 14 of the device 12 and a handle cover 58 of the tray 50 for enclosing the handle 18 of the device 12. Furthermore, the line 54 causes the tray 50 to be frangible along line 54. As shown best in FIG. 5, the line 54 scribed across the raised portion of the tray 50 is positioned over the hub 16 and handle 18 of the device 12 so as to allow the handle 18 to be fully exposed to finger access when the tray 50 is broken open at the line 54 and angularly deformed as shown in FIG. 5. Furthermore, the line 54 is also positioned so as to maintain the needle portion 14 of the venipuncture device 12 fully enclosed within the needle cover 56 of the tray 50 when the package 10a is opened.

It should also be noted in connection with FIG. 5 that when the package 10a is opened, the opening 62 is large enough to permit the venipuncture device 12 to be withdrawn or inserted into the needle cover 56 of the tray 50 without having to apply any significant force to remove the needle cover 56 which encloses the needle 14 of the device 12. The device 12 may be prevented from slipping into the needle cover 56 by hooking the hub 16 of the device 12 on the fold 61. Alternatively, a hub-supporting restrictor (not shown in FIG. 5) could be formed on the backing 52 or the cover 56 to prevent the needle 12 from falling too far into the needle cover 56. For example, one such suitable hub-supporting restrictor would be the handle restraining portion 34 described previously in connection with FIG. 1. In this manner, complete finger access to the handle 18 of the device 12 is maintained at all times while the package 10a is opened.

As further illustrated in FIG. 4, the tray 50 also has a flange 64 which circumscribes the entire raised portion of the tray 50. The flange 64 provides a surface to which the adhesive (not shown) may be applied in order to join the paper backing 52 to the bottom of the tray 50. The surface-engaging ends 66 and 68 defined by the flange 64 at the leading and trailing ends of the package 10a are used to support the package 10a in its angularly deformed position as shown in FIG. 5.

In order to use the package 10a illustrated in FIGS. 4 and 5 as a combination needle cover and venipuncture device tray, it is only necessary to bend the package 10a in the vicinity of the line 54 scribed across the periphery of the raised portion of the blister cover 50. In doing so, the blister cover 50 will break open along the line 54. It should be noted that the embodiment of FIGS. 4 and 5 is particularly adaptable for use with a venipuncture device 12 having a resilient plastic handle 18 such as that provided with the Vinca II manufactured by Sorenson Research Co., Inc. as described in the initial portion of the specification. Thus, as the handle cover 58 of the tray 50 is bent downward, the handle 18 of the venipuncture device 12 will also bend until the handle 18 has been freed from the handle cover 58. The handle 18 will then return to its normal position as shown in FIG. 18. In this manner, the package 10a may be broken open and angularly deformed as shown in FIG. 5 so as to fully expose the handle 18 of the venipuncture device to finger access while maintaining the needle portion 14 enclosed within the package 10a. Furthermore, when supported in the upright position as shown in FIG. 5, the device 12 may be easily withdrawn or reinserted with only one hand into the needle cover 56 of the tray 50.

3. Method and Structure of the Embodiment of FIGS. 6–8

Figure 6:
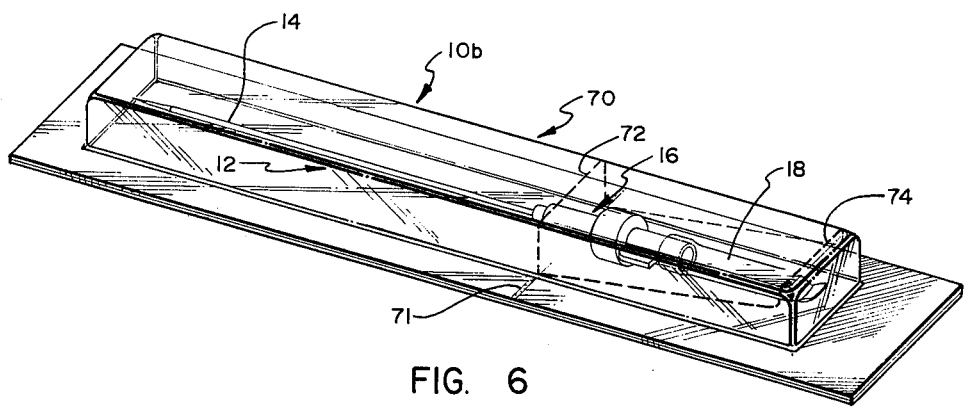
FIG. 6 is a perspective view of a third embodiment of the present invention.
Figure 7:
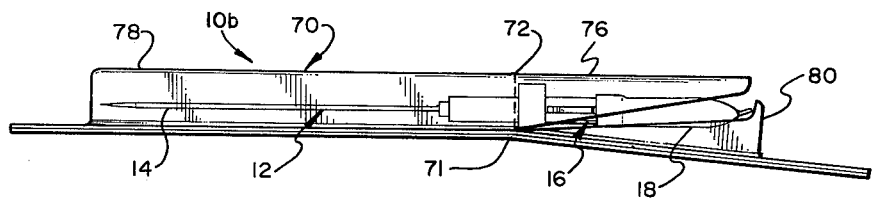
FIG. 7 is a side elevational view showing the embodiment of FIG. 6 in a partially open state.
Figure 8:
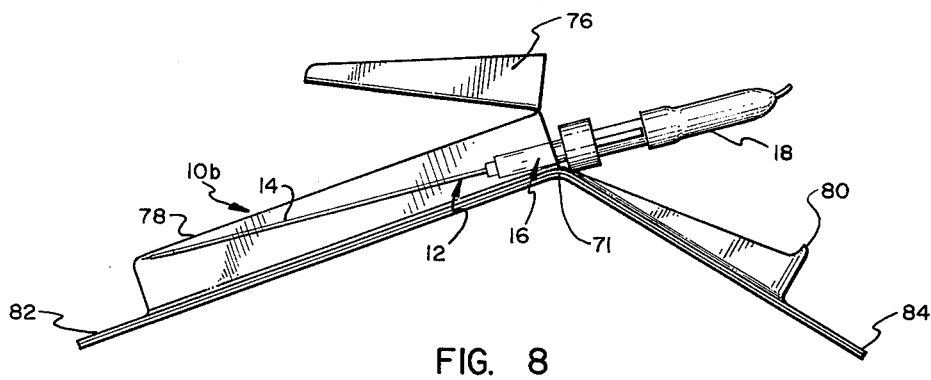
FIG. 8 is a side elevational view showing the embodiment of FIG. 6 being completely open and angularly deformed so as to permit its use as a combination needle cover and venipuncture device tray.

The embodiment of package 10b shown in FIGS. 6–8 differs from that of package 10a shown in FIGS. 4 and 5 only in the manner in which the tray generally designated 70 is broken open. From FIG. 6, it will be noted that two continuous lines 72 and 74 have been scribed across the surface of the raised portion of the tray 70 thereby defining a middle portion 76 on the tray 70 which may be removed.

In order to use the package 10b as a combination needle cover and venipuncture device tray, the package is first broken along line 74. This opens the tray 70 at line 74 as shown in FIG. 7. The middle portion 76 of the tray 70 is then bent at line 72 upwards and away from the handle 18 of the venipuncture device 12 as shown in FIG. 8. The middle portion 76 of the tray 70 may then be completely detached if desired. Alternatively, the middle portion 76 may be left in tact as shown in FIG. 8. The handle cover 80 of tray 70 is then bent completely away from the handle 18 of the venipuncture device so as to angularly deform the package 10b at fold line 71 and so as to completely expose the handle 18 to finger access as shown in FIG. 8.

Again, as with the embodiment described in FIGS. 4 and 5, the fold line of tray 70 engages the hub portion 16 of the needle 14 so as to prevent the device 12 from slipping further down into the needle cover 78 of tray 70. Also, when angularly deformed as shown, surface-engaging ends 82 and 84 support the package 10b in an upright position so as to keep the venipuncture device 50 easily accessible. The cross-sectional area of tray 70 is sufficiently large so as to allow the venipuncture device 12 to be easily withdrawn or reinserted with one hand without having to apply any significant force to remove the needle cover 78 off of the hub 16 and needle 14 of the venipuncture device 12.

It should also be noted in connection with FIGS. 6–8 that unlike the embodiment described in connection with FIGS. 4 and 5, the removable middle portion 76 of tray 70 allows package 10b to be used with a venipuncture device having a rigid handle 18.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A sterile package for venipuncture devices, said package being constructed in part of ductile material so that it can be angularly deformed when opened and comprising:

a top blister cover for the venipuncture device formed of ductile, transparent plastic, said blister cover being preformed to define a needle portion, a handle portion, and a handle restraining portion disposed between the needle portion and the handle portion, said handle restraining portion having a generally parabolic cross-sectional shape of smaller transverse and longitudinal dimensions than said needle and handle portions, said parabolically shaped handle restraining portion also defining a communicating passageway between said needle and handle portions, the needle portion and handle portion also each having a sloped surface that joins the parabolically cross-sectional shaped handle restraining portion so as to converge at the base of the handle restraining portion, thereby defining a bending location at said handle restraining portion which facilitates angular deformation of the top blister cover into an upright tray which fully exposes the handle of the device to finger access after bending the package, said handle restraining portion also defining an opening to the needle portion of the cover of sufficient diameter so as to allow withdrawal of the device without applying significant force to remove the blister cover when it is angularly deformed, said blister cover also having a peripheral flange circumscribing the base of the blister cover and defining front and rear surface-engaging edges for supporting the blister cover on a flat surface after it has been angularly deformed;

a flat strip of paper peelably joined to the blister cover so as to completely enclose the entire venipuncture device within the blister cover, said strip being peeled away from the handle portion of the blister cover and the handle restraining portion of the blister cover so as to partially expose the handle of the venipuncture device to finger access while at the same time maintaining the needle of the venipuncture device enclosed within the sterile needle portion of the blister cover, said handle of the venipuncture device being completely exposed to unobstructed finger access only after the blister cover has been angularly deformed; and adhesive means disposed between the blister cover and strip of paper for peelably joining the blister cover to the paper, thereby forming a normally closed package for enclosing the entire venipuncture device until such time as the paper is peeled away from the handle portion and handle restraining portion of the blister cover so as to partially expose the handle of the venipuncture device in order to accommodate withdrawal of the device from the package.

2. A method of accessing a venipuncture device from a package, the package having a preformed blister cover and a closure strip peelably joined to the blister cover, said blister cover being formed so as to define a needle portion, a handle portion and a handle restraining portion disposed between the needle portion and the handle portion, said handle restraining portion having a generally parabolic cross-sectional shape of smaller transverse and longitudinal dimensions than said needle and handle portions, said parabolically shaped handle restraining portion also defining a communicating passageway between said needle and handle portions, the needle and handle portion also each having a sloped surface that joins the parabolically cross-sectional shaped handle restraining portion and that converges at the base of the handle restraining portion, thereby defining a bending location at said handle restraining portion, the method comprising the steps of:

peeling said closure strip away from said handle and handle restraining portions so as to expose essentially only the handle of the venipuncture device;

bending said package at the bending location defined on said package so as to expose essentially the entire handle of said device to finger access without exposing the needle of said device, thereby also forming a device tray which is self-supporting in an upright position;

placing the bent package in an upright position upon an essentially level surface; and removing the venipuncture device from the package.

3. A method as defined in claim 2 further comprising the steps of:

restraining the handle of the venipuncture device by said handle restraining portion of the blister cover when the blister cover has been angularly deformed, thereby preventing the handle of the device from slipping back into the blister cover after the blister cover has been angularly deformed; and presenting a guide for the needle of the venipuncture device, said guide being defined at least in part by the handle restraining portion of the deformed blister cover.

4. A sterile package for venipuncture devices, said package being constructed in part of ductile material so that it can be angularly deformed when opened and comprising:

a top blister cover made of ductile, transparent plastic, the blister cover having a single raised portion that covers the entire venipuncture device, said raised portion having a cross-sectional size which will permit the device to be withdrawn from the blister cover with one hand without having to apply any significant force to remove the cover when opened, said blister cover also having a peripheral flange formed so as to circumscribe the base of the raised portion, said flange having a fold line scribed thereon to facilitate bending of said peripheral flange at the fold line, said flange also defining front and rear surface-engaging ends that support the package on a flat surface after it has been angularly deformed, said blister cover also having a plurality of score lines scribed across the surface of the raised portion of the blister cover so as to facilitate breaking said raised portion open along said score lines when the blister cover is angularly deformed, said score lines converging at said fold line and defining a detachable section of said raised portion of blister cover, said detachable section being located on the raised portion of the blister cover so as to permit essentially only the handle of said venipuncture device to be fully exposed when the package is angularly deformed;

a flat cover joined to the peripheral flange of said blister cover, said flat cover enclosing the venipuncture device within the blister cover; and means disposed between the blister cover and the flat cover for adhesively joining the flat cover to the blister cover.

5. A method of opening a package which encloses a venipuncture device, the package having a raised blister cover and a closure strip joined to the blister cover and enclosing the device therewithin, said blister cover having a peripheral flange with a fold line scribed thereon, and said blister cover further having a plurality of score lines scribed on the blister cover so as to converge with said fold line, thereby defining a detachable section of said blister cover, the method comprising the steps of:

breaking said blister cover open along a first score line in the vicinity of the handle;

bending said closure strip and said peripheral flange of said blister cover at said fold line into an angular configuration;

breaking the blister cover open along a second score line so as to permit removal of said detachable section of blister cover;

placing said package in an upright position upon an essentially level surface; and removing the venipuncture device from said package.

* * * * *